(12) United States Patent
Leavitt et al.

(10) Patent No.: US 6,540,682 B1
(45) Date of Patent: Apr. 1, 2003

(54) PORTABLE, CONFIGURABLE AND SCALABLE ULTRASOUND IMAGING SYSTEM

(75) Inventors: Steven C Leavitt, East Boothbay, ME (US); Joseph R Fallon, Boxford, MA (US); Michael P Anthony, Andover, MA (US); Theodore P Fazioli, Salem, NH (US); Charles R Dowdell, Nashua, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 39 days.

(21) Appl. No.: 09/710,985

(22) Filed: Nov. 9, 2000

(51) Int. Cl.⁷ .................................................. A61B 8/00
(52) U.S. Cl. ...................................... 600/447; 600/443
(58) Field of Search ................................. 600/437, 447, 600/443, 455, 438, 449; 73/625, 626

(56) References Cited

U.S. PATENT DOCUMENTS

| | | |
|---|---|---|
| 5,590,658 A | 1/1997 | Chiang et al. |
| 5,603,323 A | 2/1997 | Pflugrath et al. |
| 5,636,631 A | 6/1997 | Waitz et al. |
| 5,690,114 A | 11/1997 | Chiang et al. |
| 5,715,823 A | 2/1998 | Wood et al. |
| 5,722,412 A | 3/1998 | Pflugrath et al. |
| 5,817,024 A | 10/1998 | Ogle et al. |
| 5,839,442 A | 11/1998 | Chiang et al. |
| 5,851,186 A | 12/1998 | Wood et al. |
| 5,879,303 A | 3/1999 | Averkiou et al. |
| 5,891,035 A | 4/1999 | Wood et al. |
| 5,893,363 A | 4/1999 | Little et al. |
| 5,897,498 A | 4/1999 | Canfield et al. |
| 5,938,607 A | 8/1999 | Jago et al. |
| 5,957,846 A | 9/1999 | Chiang et al. |
| 5,964,709 A | 10/1999 | Chiang et al. |
| 5,997,479 A | 12/1999 | Savord et al. |
| 6,007,490 A | 12/1999 | Pawluskiewicz |

(List continued on next page.)

OTHER PUBLICATIONS

Terason 2000 information obtained from url: www.terason.com/terason2000.htm; 6 pages.
Sonosite 180 information obtained from url: www.sonosite.com/products_180_heart.html; 5 pages.
SonoHeart Applications Summary obtained from the SonoSite brochure; 2 pages.

*Primary Examiner*—Marvin M. Lateef
*Assistant Examiner*—Ruby Jain
(74) *Attorney, Agent, or Firm*—John Vodopia

(57) ABSTRACT

A portable, configurable and scalable ultrasonic imaging system uses a phased ultrasonic transducer array coupled to a portable, configurable and scalable ultrasonic processor to develop ultrasonic images. When used in conjunction with a sector phased array, the portable, configurable and scalable ultrasonic imaging system uses a processing channel associated with each element in the transducer array to develop the ultrasonic image. When used with a linear or curved linear transducer array, the portable, configurable and scalable ultrasonic processor uses fewer processing channels than transducer elements to develop the ultrasonic image. Since the portable, configurable and scalable ultrasonic processor is scalable, it is able to use a variety of processors, software and transducer arrays to develop a number of different ultrasonic output images. The portable, configurable and scalable ultrasound imaging system includes a scalable architecture and includes alternative software configurable imaging applications and operating modes, and includes modifiable processing algorithms and operating features.

39 Claims, 4 Drawing Sheets

U.S. PATENT DOCUMENTS

| | | |
|---|---|---|
| 6,013,032 A | 1/2000 | Savord |
| 6,102,863 A | 8/2000 | Pflugrath et al. |
| 6,106,468 A | 8/2000 | Dowdell |
| 6,106,472 A | 8/2000 | Chiang et al. |
| 6,113,547 A | 9/2000 | Catallo et al. |
| 6,117,084 A | 9/2000 | Green et al. |
| 6,117,085 A | 9/2000 | Picatti et al. |
| 6,135,961 A | 10/2000 | Pflugrath et al. |
| 6,312,381 B1 * | 11/2001 | Knell et al. .................. 600/437 |
| 6,436,039 B1 * | 8/2002 | Lannutti et al. ............. 600/437 |

* cited by examiner

PORTABLE, CONFIGURABLE AND SCALABLE ULTRASOUND IMAGING SYSTEM

TECHNICAL FIELD

The invention relates generally to ultrasound imaging systems, and, more particularly, to a portable and configurable ultrasound imaging system.

BACKGROUND OF THE INVENTION

Ultrasound imaging systems have been available for quite some time and are commonly used in nondestructive testing and medical applications. Medical ultrasound imaging allows the internal structure of the human body to be viewed non-invasively in real time. Preferably, the imaging system is portable, allowing the system to be used in applications requiring mobility, such as hospital emergency rooms, hospital rounds and private practice applications. Furthermore, the imaging system should be inexpensive to meet the budget constraints of the medical industry and should require minimal power to allow for battery operation necessary in some of the above applications.

In the past, ultrasonic imaging systems consisted of a large and bulky processing and display unit connected to an ultrasonic probe assembly using a cable. The probe assembly contained the ultrasonic transducers that are used to transmit interrogating pulses and receive reflected ultrasonic energy from the target. The processing and display unit contained all the processing systems and a display on which the image is presented to the user. Unfortunately, these processing and display systems were not easily adaptable to different end user needs. These prior systems typically required extensive re-engineering to accommodate different end user needs. The systems were designed using multiple printed circuit boards with complex interactions that necessitated significant re-engineering to address the varied market needs.

As ultrasonic imaging systems were developed further, electronic integration and miniaturization allowed the systems to become smaller in size. These smaller units may divide some of the processing functionality between the probe assembly and the main processing and display unit. Unfortunately, even these smaller systems remain difficult to adapt to different transducer arrays, processing techniques or software enhancements.

Therefore, it would be desirable to have a portable ultrasonic imaging system that can be easily configured for a variety of transducer array types and processing techniques and that easily accommodates processor and software enhancements.

SUMMARY OF THE INVENTION

The invention provides a portable and configurable ultrasound imaging system that can be easily configured to support a variety of transducer arrays and processing techniques and that easily allows processor and software enhancements. The portable, configurable ultrasound system incorporates the use of various transducer arrays and beamforming circuitry to process received ultrasonic energy into a viewable image. The ultrasound system includes a portable, configurable processor that includes a modular processor and a modular memory element. The modularity of the system design both in software and hardware facilitates system upgrades and enhancements with minimal impact to other aspects of the system design. An example of the modularity is the use of a unified memory, thus allowing system software upgrades and enhancements with minimal impact to the balance of the system. The portable and configurable ultrasound imaging system allows alternative imaging applications and operating modes and includes modifiable processing algorithms and operating features, which provide the high degree of configurability to the portable and configurable ultrasound imaging system.

BRIEF DESCRIPTION OF THE FIGURES

The components in the figures are not necessarily to scale relative to each other, emphasis instead being placed upon clearly illustrating the principles of the invention. Moreover, in the figures, like reference numerals designate corresponding parts throughout the different views.

DETAILED DESCRIPTION

Although the invention will be described below with particular reference to sector phased transducer array technology, the invention is applicable to ultrasonic imaging systems using any type of transducer array technology.

Figure 1:
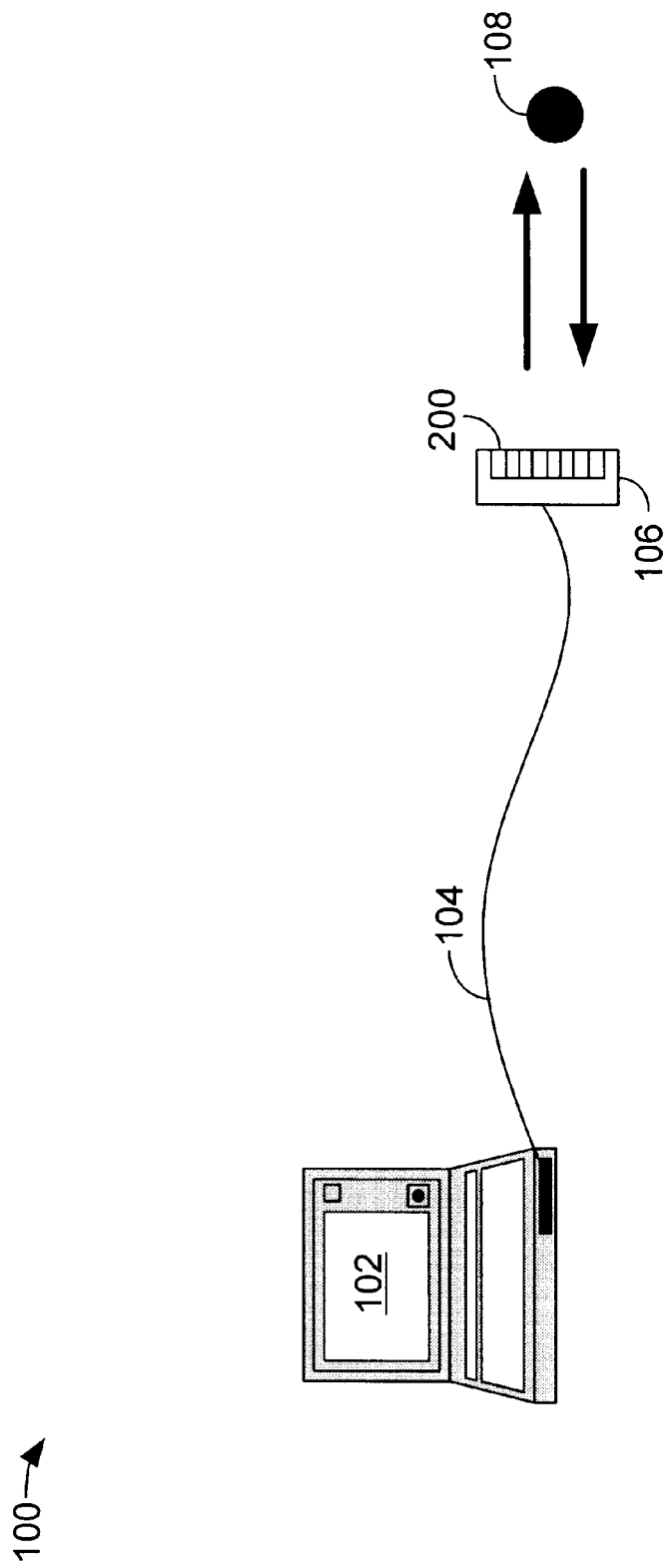
FIG. 1 is a graphical view illustrating a portable, configurable ultrasound system constructed in accordance with an aspect of the invention.

Turning now to the drawings, FIG. 1 is a graphical view illustrating a portable, configurable ultrasound system 100 constructed in accordance with an aspect of the invention. Portable, configurable ultrasound system 100 includes portable processor 102 connected via interface cable 104 to probe assembly 106. Probe assembly 106 includes sector phased transducer array 200, which transmits ultrasonic energy to target 108 and receives reflected ultrasonic energy from target 108. The portable, configurable processor 102 processes the received ultrasonic energy.

After processing, a two-dimensional (2-D) image generated from the received ultrasonic energy is then displayed on a liquid crystal display (LCD) incorporated within portable, configurable processor 102. Probe assembly 106 may include additional processing circuitry that enables some of the ultrasound energy received from target 108 to be processed into a number of sub-beams. These sub-beams represent the energy received from all of the transducers in probe assembly 106 using a number of signals less than that of the number of transducer elements. Sub-beamforming reduces the number of signals that must be communicated between probe assembly 106 and portable processor 102 via interface cable 104. Such a system is disclosed in commonly assigned, copending U.S. patent application, entitled SUB-BEAMFORMING APPARATUS AND METHOD FOR A PORTABLE ULTRASOUND IMAGING SYSTEM, assigned Ser. No. 09/687,252 and filed on Oct. 13, 2000 the text of which is incorporated into this document by reference.

Furthermore, the probe assembly, including a methodology for sub-beamforming using analog signal processing, is disclosed in commonly assigned U.S. Pat. No. 6,013,032, issued on Jan. 11, 2000 to Savord, and in commonly assigned U.S. Pat. No. 5,997,479, issued on Dec. 7, 1999, to Savord et al., the text of both patents being incorporated into this document by reference. The probe assembly 106 may also contain one or more transmit application specific integrated circuit(s) ASIC(s), which provide transmit high voltage pulses to the transducer array 200 contained within probe assembly 106.

Figure 2:
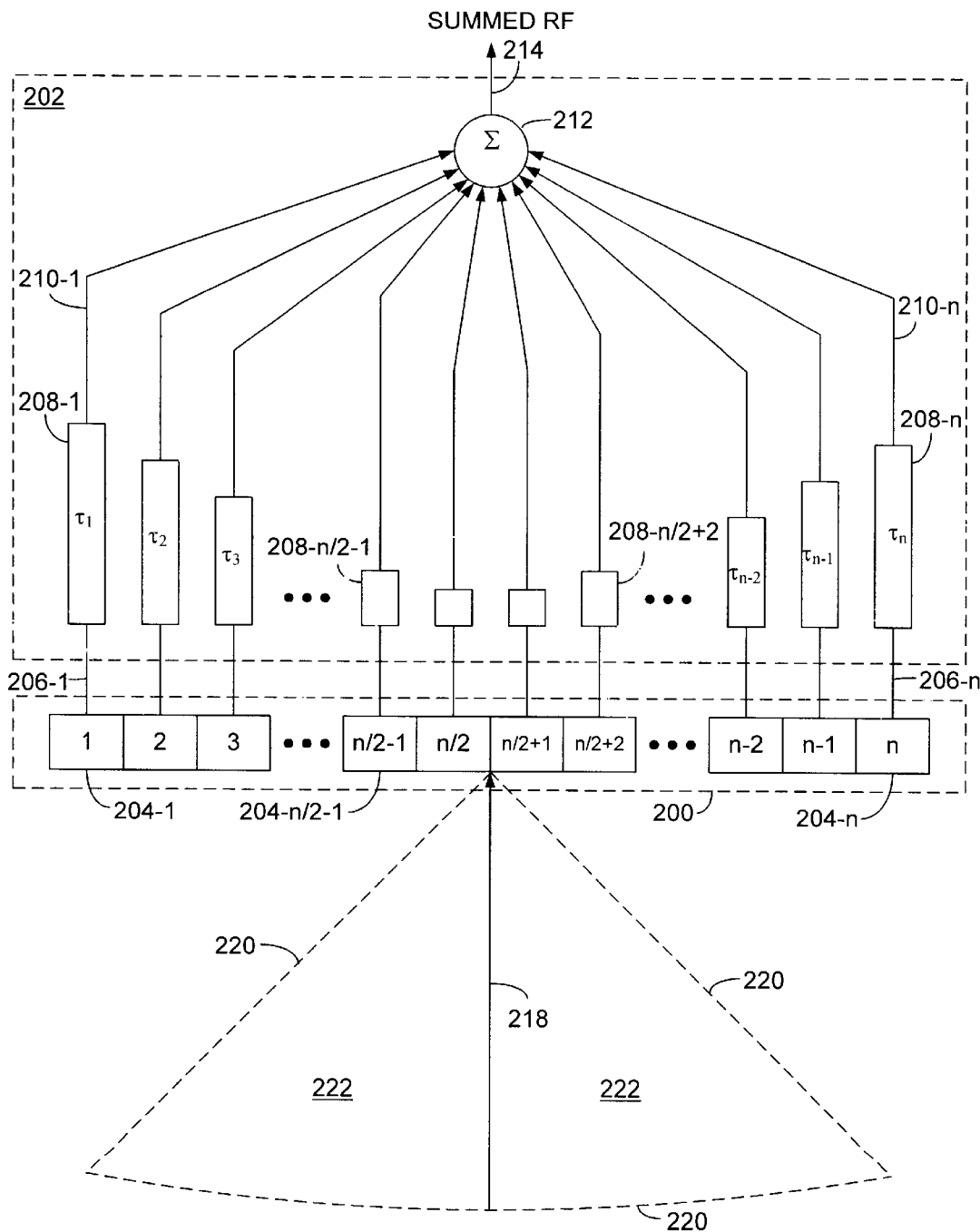
FIG. 2 is a simplified schematic diagram illustrating a sector phased transducer array located in the probe assembly and a phased array beamformer located in the portable, configurable processor 102 of FIG. 1.

FIG. 2 is a simplified schematic diagram illustrating a sector phased transducer array 200 located in probe assembly 106 (FIG. 1) and a phased array beamformer 202 located in the portable, configurable processor 102 (FIG. 1). Phased array beamformer 202 includes a delay structure suitable for illustrating the functional aspect of a sector phased array beamformer as contrasted with the alternative sub-beamformer approach mentioned above in U.S. Patent Application Ser. No. 09/687,252 entitled SUB-BEAMFORMING APPARATUS AND METHOD FOR A PORTABLE ULTRASOUND IMAGING SYSTEM, in U.S. Pat. No. 6,013,032, and in U.S. Pat. No. 5,997,479, mentioned above.

Transducer array 200 is a sector phased array ultrasonic transducer. Transducer array 200, as shown in FIG. 2, includes an n-element sector phased array, which includes a plurality of individual transducer elements 204-1 through 204-n. Each of the transducer elements 204-1 through 204-n connects to a corresponding delay element 208-1 through 208-n via a plurality of corresponding connections 206-1 through 206-n. The delay elements 208-1 through 208-n form a receive beam for a representative central receive line (also referred to as a sector scan line) 218 shown in FIG. 2. The delay elements for this one particular sector scan line 218 are symmetrical about the center of the transducer array 200. Delay element 208-1 would equal delay element 208-n and delay element 208-n/2−1 would equal delay element 208-n/2+2. The delays from the outermost element 204-1 to the central elements, such as delay element 204-n/2−1, decrease in a monotonic manner due the reduced delays needed as the elements become increasingly closer to the sector scan line 218 and, hence, to the receive target (108 of FIG. 1). Because there is no symmetry for non-center lines, a unique delay path is associated with each element 204-1 through 204-n.

Each of the delay elements 208-1 through 208-n connects via corresponding connections 210-1 through 210-n to a summing element 212. The output of summing element 212 on connection 214 is the summed RF energy received from each ultrasonic transducer element 204-1 through 204-n. The connections 206-1 through 206-n are typically contained in the interface cable 104, while the phased array beamformer 202 is typically located in the portable, configurable processor 102 shown in FIG. 1. However, the phased array beamformer 202 could be partitioned as a sub-beamformer with the sub-beamformers contained within the probe assembly 106 (FIG. 1). In such an arrangement, a reduced set of connections formed by the sub-beamformer outputs would be contained in cable 104 shown in FIG. 1. It should be noted that, while described above using a sector phased array, the invention can be implemented using other types of phased arrays, linear arrays, or curved linear arrays.

During operation, the n-element sector phased array 200 electronically steers and focuses a beam of ultrasonic energy to interrogate the sector defined using reference numeral 222 and bounded by the perimeter of the sector defined by line 220. The sector 222 is representative of a typical region interrogated by a number of successive ultrasonic transducer pulses using a sector phased transducer array 200. The region of interest using the sector phased transducer array 200 could be defined with a variety of different shapes. For example, the shape could be an asymmetrical sector with more scan lines on one side of the center than on the other. The shape could be a triangular shape exhibiting no radius of curvature at the deepest depth. Also, as previously noted, the array may not be a sector phased array but may be a curved linear array (CLA) or a linear array. Such arrays lead to regions of interest such as a sector of an annulus, rectangular, rectangular with extended sector sides, and a number of other regions that are well known in the art.

Typically, for a sector phased array, 100 or more separate scan lines, an exemplar one of which is illustrated as sector scan line 218, are used to interrogate the region of interest indicated by sector 222. After the focused transmit pulse is used to interrogate a particular scan direction, the receive line following the transmit interrogation representing the ultrasonic energy received from the target 108 (FIG. 1), is received by the n-element sector phased array 200. A typical transmit/receive scan line is shown in FIG. 2 as sector scan line 218. Importantly, the arrangement of the n-element sector phased array 200 assures that each ultrasonic transducer element 204-1 through 204-n is associated with its own corresponding delay channel. These delayed signals are summed in summing element 212 to develop the summed RF signal on connection 214.

Figure 3:
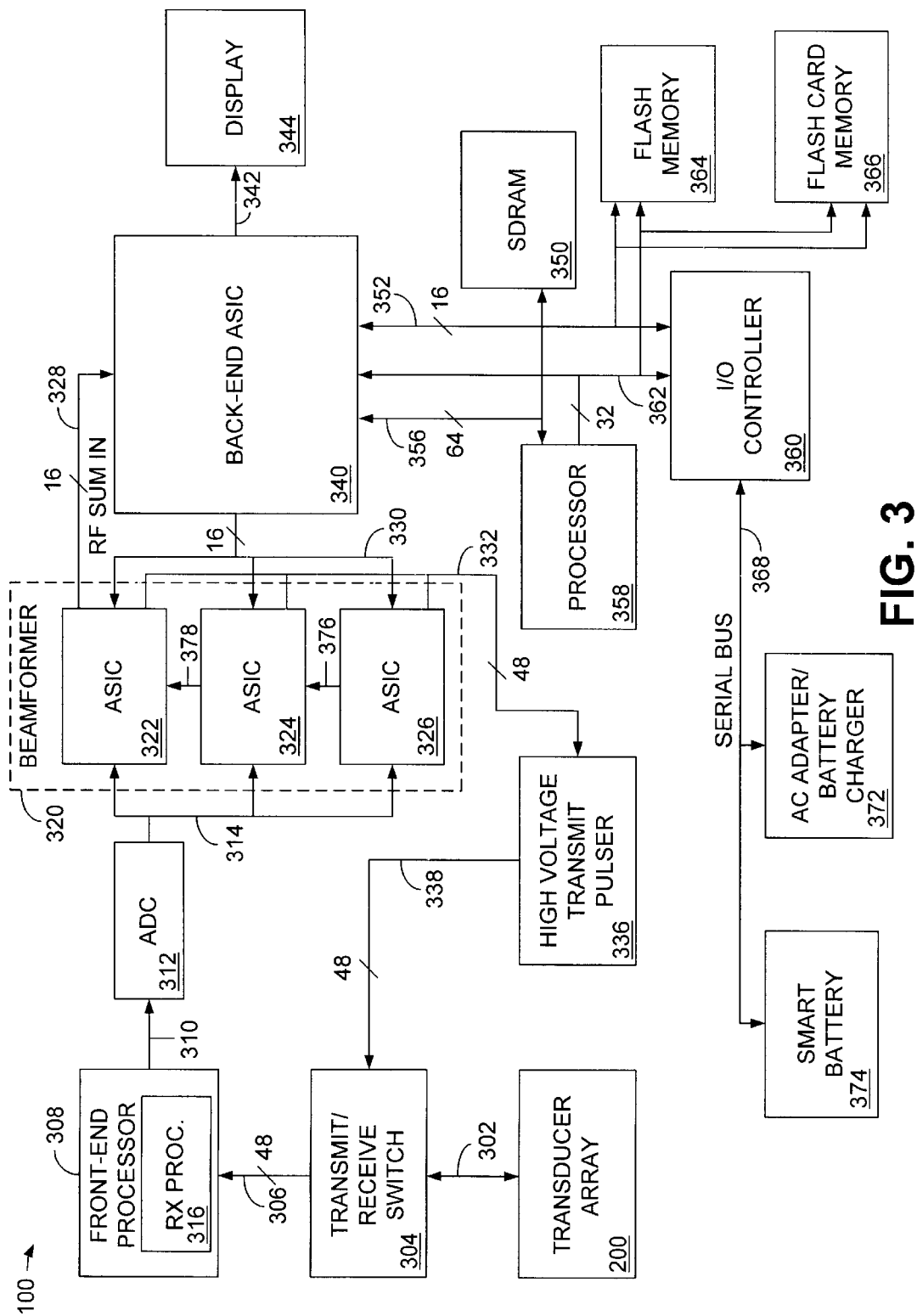
FIG. 3 is a block diagram illustrating the portable, configurable ultrasound system of FIG. 1.

FIG. 3 is a block diagram illustrating the portable, configurable ultrasound system 100 of FIG. 1. The portable, configurable ultrasound system 100 includes sector phased array 200, which communicates with transmit receive (T/R) switch 304 via connection 302. In one embodiment, the sector phased array 200 is located in probe assembly 106 (FIG. 1) and the connection 302 of FIG. 3 is contained within interface cable 104 of FIG. 1. T/R switch 304 isolates the transmit pulses from the received ultrasound energy and delivers the received signals (one for each transducer element) via connection 306 to processor 308. Processor 308 is typically referred to as a "front-end" processor.

Illustratively, sector phased array 200 includes 48 transducer elements, resulting in 48 signal channels. However, the sector phased transducer array 200 may include more or fewer transducer elements. Furthermore, while illustrated using a single block in FIG. 3, the front-end processor 308 may be implemented as one or more ASICs. The T/R switch 304 also functions as an isolation circuit, thus preventing transmit energy supplied by high voltage transmit pulser 336 via connection 338 (to be described below) from migrating via connection 306 to the sensitive front-end processor 308. The front-end processor 308 includes a receive processor 316, which receives the ultrasonic energy signals from each transducer element 204-1 through 204-n within sector phased transducer array 200 and performs amplification and filtering of the received signals.

The output of front-end processor 308 is supplied via connection 310 to analog-to-digital converter (ADC) 312. ADC 312 digitizes the samples for each channel on connection 310 and supplies an 8-bit digital bit stream for each channel via connection 314 to beamformer 320. The appropriate channels on connection 314 are supplied to each ASIC 322, 324 and 326 within beamformer 320. While illustrated using three ASICs 322, 324 and 326 in a cascaded arrangement, more or fewer ASICs may be used within beamformer 320 depending upon the number of transducer elements (and corresponding channels) within transducer array 200 and associated with each ASIC.

Each of the ASICs 322, 324 and 326 also provides the low voltage transmit timing signal via connection 332 to drive the high voltage transmit pulser 336. Although illustrated using a single block, there is one high voltage transmit pulser 336 used to drive each transducer element 204-1 through 204-n (FIG. 2). Furthermore, the low voltage transmit pulser signal function and/or the high voltage transmit pulser may be incorporated into one or more ASICs. Further still, the T/R switch 304, front-end processor 308 and the high voltage transmit pulser 336 may also be incorporated, in any combination, into one or more ASICs.

Each of the ASICs 322, 324 and 326 within beamformer 320 processes 16 of the 48 signals corresponding to the 48 channels received from sector phased array 200. Because each ASIC processes only 16 channels, each ASIC supplies a digital intermediate RF sum signal containing the channels processed therein to another ASIC until the last ASIC in the beamformer 320 is reached. For example, ASIC 326 supplies a 16 bit intermediate RF sum digital output via connection 376 to ASIC 324, and ASIC 324 provides its 16 bit intermediate RF sum (including 32 channels) digital output via connection 378 to ASIC 322. The combined output of the beamformer 320 is then taken from ASIC 322 via connection 328 and supplied as the 16-bit beamformed signal to the processor 340 as the signal "RF SUM IN." The processor 340 is typically referred to as a "back-end" processor and is typically implemented in one or more ASICs and is therefore typically referred to as a back-end ASIC. For purposes of illustration, a single beamformer is used. However, a parallel beamformer can easily be implemented by having a parallel set of beamformer ASICs (or add parallel processing within the current ASICs) share the outputs of the ADC 312. The result is two separate beamformer outputs that are capable of independently beamforming two separate receive beams. The use of parallel beams offers advantages such as increased frame rates.

Back-end ASIC 340 performs many processing functions and will be described in greater detail with respect to FIG. 4. Back-end ASIC 340 also provides to beamformer 320, via connection 330, the coefficient data that allows each of the ASICs 322, 324 and 326 within beamformer 320 to perform the beamfonning function and to perform the transmit timing necessary to generate the low voltage transmit signal timing pulses on connection 332.

The high voltage transmit pulser 336 can be implemented using discrete components or in an ASIC. In either arrangement, the low voltage transmit timing signals are taken from beamformer 320 via connection 332 and supplied to high voltage transmit pulser 336. Transmit pulser 336 then supplies the 48 transmit pulses via connection 338 to T/R switch 304. T/R switch 304 routes these transmit pulses via connection 302 to each corresponding transducer element 204-1 through 204-n within sector phased array 200. For parallel receive beamformers, the transmit beam would be broadened by appropriate low voltage transmit timing signals allowing parallel adjacent receive beams to be formed from a single transmit beam.

Back-end ASIC 340 processes the RF SUM IN signal supplied via connection 328 and provides the ultrasonic image via connection 342 where it is displayed on display 344. Display 344 can be a liquid crystal display (LCD) or any other display capable of displaying the ultrasonic image data. Back-end ASIC 340 also communicates with memory element 350 via bi-directional data bus 356. Memory element 350 is a static/dynamic random access memory element, preferably 32-megabytes or greater in size, and is preferably implemented as a unified memory as described in commonly assigned U.S. Pat. No. 6,106,468 issued on Aug. 22, 2000 to Dowdell, the text of which is incorporated into this document by reference. The memory element 350 is used for intermediate data storage, storing processing code, tables, and all other executable software used by back-end ASIC 340.

Back-end ASIC 340 also communicates with processor 358 via bi-directional data bus 356. Processor 358 is preferably a 7xx series processor sold under the trademark POWERPC, which is a registered trademark of Motorola Corporation. However, any other processor suitable for processing the received ultrasonic signals can be used. Processor 358 communicates with the back-end ASIC 340, memory element 350, flash memory element 364 and the flash card memory 366 via address bus 362, which is, for example purposes, 32 bits wide. In accordance with an aspect of the invention, the memory element 350 and the processor 358 are external from the ASICs and modularly implemented, whereby they are scaleable, upgradeable and interchangeable without significant system impact. For example, the memory element 350 can be upgraded without impacting any other element within the portable, configurable ultrasound system 100. Similarly, the processor 358 can be upgraded without impacting any other element within the portable, configurable ultrasound system 100. Furthermore, the processor 358 uses standard personal computer (PC) tools and compilers. As used herein, the term modular indicates that neither the processor 358 nor the memory element 350 is embedded in an ASIC device. In this manner, the portable, configurable ultrasound system 100 can be upgraded with minimal system impact. By not incorporating these elements within an ASIC, rapid and easy memory and computational upgrades are possible without necessitating an expensive and time consuming ASIC redesign.

Upgradability allows for alternative imaging applications beyond the current cardiac focus such as abdominal, obstetrical, gynecological, vascular and small parts. Even the use of a transesophageal echo (TEE) is possible with upgradeable software and a TEE probe. The system also allows for alternative operating modes. For example, as known by those skilled in the art, alternative scanning formats, such as line splicing can be incorporated into the portable, configurable ultrasound system to achieve a composite receive line from multiple transmit lines where each transmit line has a different focal point achieved through aperture and pulse shaping. Furthermore, other scanning formats include sector scanning, curved linear scanning and linear scanning formats and alternative aperture modes include full, split, parallel, and non-parallel, or any combination thereof. Due to the upgradability of the software and designed-in flexibility of the hardware, such as clocking agility including modifiable frequency output and the use of a connectorized transducer, multiple transducers with modifiable operating frequencies can be used. Furthermore, the unified memory element 350 makes possible the use of software controlled, modifiable memory based gamma correction.

An embodiment of the invention also includes a software algorithm for implementing color flow mapping. The color flow algorithm demonstrates the flexibility of the configurable design. Angiography imaging using a power doppler approach is also easily implemented with the current design. Angiography imaging is a derivative of the color flow mapping algorithm. The combination of being able to change the software easily in the field and the unified main memory allow easy software upgrades. All such software is contained in the memory element 350 and executed in the processor 358.

An embodiment of the invention can also be software upgraded to perform pulsed wave doppler imaging, since the necessary components, such as quadrature accumulators for the in-phase and quadrature phase channels, are incorporated in the backend ASIC 340.

The back end ASIC communicates with the UO controller, flash memory element 364 and flash card memory 366 via a bi-directional data bus 352, which is, for example, 16 bits wide. I/O controller 360 controls the input and output tasks of the portable, configurable ultrasound system 100. For example, I/O controller 360 includes a keyboard input for communicating information into the portable, configurable ultrasound system 100, and includes serial and parallel ports for the connection of peripheral devices (not shown). Flash memory element 364 is a non-volatile memory that is used to store the current executable software files (sometimes referred to as the "run-time code") that enable the ultrasound system 100 to function. Flash card memory 366 is a removable storage media and is used to conveniently update the operating system executed by the portable, configurable ultrasound system 100. Furthermore, the portable, configurable ultrasound system 100 uses modifiable processing algorithms to perform different imaging applications, scanning formats, operating modes and aperture modes. These modifiable processing algorithms are implemented in software, which is stored in memory element 350 and executed by processor 358. The modifiable processing algorithms are in modular format and can be updated through the use of flash card memory 366 through the I/O controller 360. In this manner, software upgrades can be supplied to the ultrasound system 100 and stored in flash memory element 364 by using simple, transportable flash card memory element 366.

I/O controller 360 also communicates via serial bus 368 with smart battery 374 and alternating current (AC) adapter/battery charger 372. AC adapter/battery charger 372 provides power to the portable, configurable ultrasound system 100 and charges the smart battery 374. In addition, the portable, configurable ultrasound system 100 may include a separate stand-alone battery charger (not shown) for charging the smart battery when the battery is not installed in the system. The serial bus 368 also allows the connection of test and diagnostics equipment through the I/O controller 360. By using the serial bus 368, the memory element 350, internal processor registers of processor 358 as well as internal registers in all ASICs 322, 324, 326, 340, etc., can be interrogated using an external testing device using a Joint Test Access Group (JTAG) interface. JTAG is an IEEE standard (1149.1) known as the Standard Test Access Port and Boundary Scan Architecture, and is used to provide testability for fine pitch, high pin count packages such as ASICs and processors. Those having ordinary skill in the art are familiar with the JTAG standard.

Figure 4:
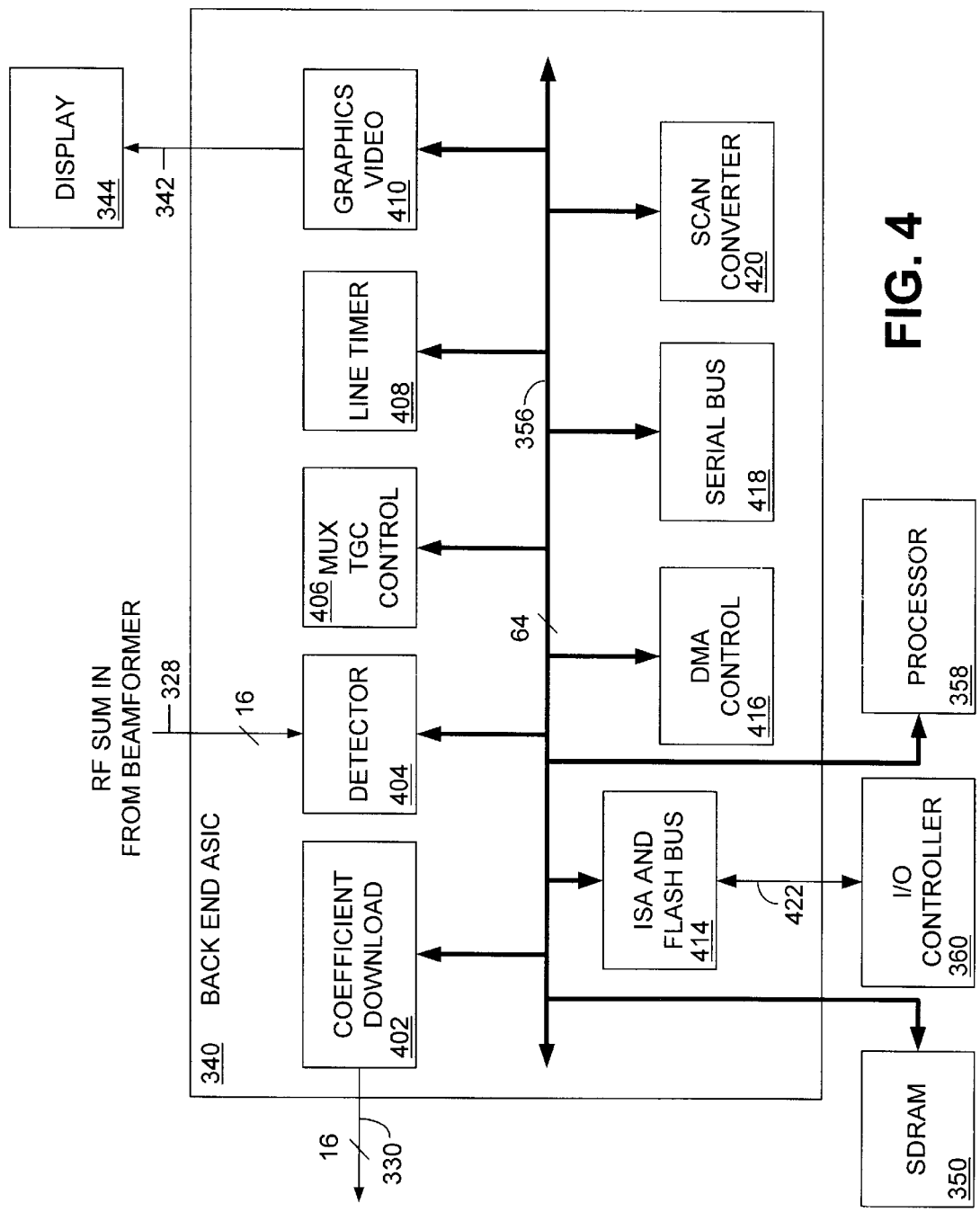
FIG. 4 is a block diagram illustrating the back-end processor of FIG. 3.

FIG. 4 is a block diagram illustrating the back-end ASIC 340 of FIG. 3. Back-end ASIC 340 includes coefficient download element 402, which supplies the coefficient data used to load each of the ASICs 322, 324 and 326 within beamformer 320 (FIG. 3). This data allows the ASICs in the beamformer 320 to perform the beamforming function on the received signal and to provide the low voltage transmit signal timing information as described above.

The beamformed digital signal labeled RF SUM IN is supplied to the detector 404 via connection 328. The detector 404 receives the digital signal via connection 328 and may provide, among other functions, time gain compensation (TGC). TGC is used when receiving ultrasound signals from multiple depths within the target. In such an instance, in order to compensate for the increasing time of flight with respect to depth of the ultrasonic energy, gain is typically increased correspondingly. Detector 404 also provides filtering and performs a detection function in which the input RF signal is converted to a baseband signal, while preserving the phase and amplitude information contained in the signal. Detection includes converting the RF data stream produced on connection 328 into log magnitude data sampled for two dimensional anatomical imaging as well as baseband quadrature data for use in two dimensional color flow imaging. For parallel beam formation, the detector would be replicated to process the two receive beams.

After detection, the data is in the form of log detected amplitude data for anatomic imaging and quadrature detected components (in-phase and quadrature) of the RF signal received from beamformer 320 via connection 328. This data is stored in memory element 350. The information is transferred from the detector 404 to the memory element 350 via bi-directional data bus 356. The bi-directional bus 356 is, for example, 64 bits wide.

For each sector scan line (shown typically as sector scan line 218 of FIG. 2) transmitted by the transducer array 200 (FIG. 2), a line of RF data is stored in memory element 350 as described above. This process continues with each sector scan line advanced by an amount consistent with the desired lateral resolution and spatial coverage. For example, each line transmitted by the transducer array 200 is at an angle different from the previously transmitted line. For each sector scan line 218 the detector detects the RF energy and stores the values in memory element 350 until a complete frame of data is stored within memory element 350. This data frame is referred to as an acoustic frame of data. When a complete acoustic frame is captured in memory 350, the processor 358 sets up a pointer in memory element 350 indicating the location in memory element 350 where the next acoustic frame will be written. The previous location in memory 350 (also tagged by a memory pointer) containing the latest acoustic data frame will be left intact.

After the latest acquired acoustic frame is stored in memory element 350, the scan converter 420 receives, from the processor 358, the pointer that indicates the location in memory 350 where the latest acoustic frame is stored. The scan converter 420 uses consecutive acoustic scan lines within that stored acoustic data to create a scan converted sector slice for transfer via bi-directional data bus 356 to another location in memory 350. A sector slice is defined as the image area between two adjacent acoustic scan lines. The scan converter 420 continues processing additional slices until all the acoustic data for the current acoustic frame has been scan converted. When the scan converter 420 completes the acoustic frame, an interrupt is sent to the processor 358 indicating that the scan converter 420 has completed the current acoustic frame. When the interrupt is received by the processor 358, the image frame data is read out of memory 350 in raster fashion via bi-directional data bus 356 under control of the graphics video element 410 for output via connection 342 to display 344. The graphics video element 410 combines all graphics overlays such as text and cursors with the acoustic frame concurrent with raster readout to the display via connection 342 for viewing on display 344.

The direct memory access (DMA) controller 416 acts as a gating function for all data travelling on bidirectional data bus 356. For example, the DMA controller 416 determines whether the scan converter 420 or the detector 404 can access the memory element 350. The DMA controller 416 operates as known to those having ordinary skill in the art.

The international standards architecture (ISA) and flash bus element 414 communicates via dedicated lines 422 to the external flash memory used by the I/O Controller 360. The flash memory used by the I/O Controller 360 is omitted for clarity and is used only to support the I/O Controller 360 and is not to be confused with the flash memory element 364 of FIG. 3 or the flash card memory 366. The flash memory element 364 provides non-volatile memory storage and includes the run-time software. The flash card 366 is a removable memory media and is used to change and upgrade the operating software when revisions or updates become available. Furthermore, images can be read from the back-end ASIC 340 and written to the flash card 366 for transport to other systems.

The line timer 408 represents a series of timers that are used by the processor 358 to provide timing and control functionality. Because all the functionality described with respect to FIG. 4 is timed, the line timer 408 provides this auxiliary timing function, thus off-loading that timing responsibility from the processor 358.

The multiplexer (MUX) TGC control element 406 is employed if a linear or a curved linear array transducer is used. In such a case, the multiplexer function of the MUX TGC control element 406 multiplexes each element of the linear or curved linear array. When a linear or curved linear array is used, a reduced number of elements are processed at any given time and a smaller than the whole number of elements is operational at any given time. Thus, reordering of the elements with respect to the processing channels is required, as those skilled in the art will recognize. The TGC portion of the MUX TGC control element 406 provides both front-end and back-end time gain compensation as described above. The back-end TGC is performed in the detector 404 in FIG. 4 and front-end TGC is performed in the front-end processor 308 of FIG. 3.

Furthermore, through the use of integration and the judicious selection of light weight components, the phased ultrasonic transducer array and the configurable ultrasonic processor can be constructed to weigh less than eight (8) pounds.

It will be apparent to those skilled in the art that many modifications and variations may be made to the preferred embodiments of the present invention, as set forth above, without departing substantially from the principles of the present invention. For example, the present invention can be used in conjunction with various ultrasonic transducer array technologies and different beamforming methodologies. All such modifications and variations are intended to be included herein within the scope of the present invention, as defined in the claims that follow.

What is claimed is:

1. A configurable ultrasound imaging system, comprising:
a phased ultrasonic transducer array including a plurality of transducer elements, each element configured to process an ultrasonic signal; and
a portable, configurable and scalable processor configured to receive and process each of the ultrasonic signals corresponding to each of the transducer elements into an ultrasonic image.

2. The ultrasound imaging system of claim 1, wherein the phased ultrasonic transducer array is a sector phased array.

3. The ultrasound imaging apparatus of claim 1, wherein the phased ultrasonic transducer array is a curved linear array.

4. The ultrasound imaging apparatus of claim 1, wherein the phased ultrasonic transducer array is a linear array.

5. The ultrasound imaging system of claim 1, wherein the portable, configurable and scalable processor includes a modular processor.

6. The ultrasound imaging system of claim 5, wherein the modular processor uses standard personal computer (PC) tools and compilers.

7. The ultrasound imaging system of claim 1, wherein the portable, configurable and scalable processor includes a modular memory.

8. The ultrasound imaging system of claim 1, wherein the portable, configurable and scalable processor includes a flash memory.

9. The ultrasound imaging system of claim 8, wherein the flash memory is scalable.

10. A configurable ultrasound imaging system, comprising:
a phased ultrasonic transducer array including a plurality of transducer elements, each element configured to process an ultrasonic signal; and
a portable, configurable processor configured to receive and process each of the ultrasonic signals corresponding to each of the transducer elements into an ultrasonic image, the portable, configurable processor comprising:
a scalable front end processor configured to receive each ultrasonic signal from each of the transducer elements; and
a scalable beamformer circuit configured to form the ultrasonic signals from each of the transducer elements into a beamformed signal.

11. The ultrasound imaging system of claim 10, wherein the scalable beamformer circuit is cascaded.

12. The ultrasound imaging system of claim 10, wherein the scalable beamformer circuit is configured to perform parallel beamforming.

13. The ultrasound imaging system of claim 12, wherein the scalable beamformer circuit is cascaded.

14. The ultrasound imaging system of claim 1, wherein the portable, configurable and scalable processor further comprises a scan converter capable of processing ultrasonic signals from an ultrasonic transducer array chosen from the group consisting of a sector, linear, curved linear and combination format array.

15. A configurable ultrasound imaging system, comprising:
a phased ultrasonic transducer array including a plurality of transducer elements, each element configured to process an ultrasonic signal; and
a portable, configurable processor configured to receive and process each of the ultrasonic signals corresponding to each of the transducer elements into an ultrasonic image, the portable, configurable processor comprising:
a transmit/receive switch coupled to the phased ultrasonic transducer array;
a high voltage transmit pulser coupled to the transmit/receive switch; and
a receive processor coupled to the transmit/receive switch, wherein the transmit/receive switch, the high voltage transmit pulser and the receive processor are commonly integrated on an application specific integrated circuit (ASIC).

16. A configurable ultrasound imaging system, comprising:
a phased ultrasonic transducer array including a plurality of transducer elements, each element configured to process an ultrasonic signal; and a portable, configurable processor configured to receive and process each of the ultrasonic signals corresponding to each of the transducer elements into an ultrasonic image, the portable, configurable processor comprising:
- a transmit/receive switch coupled to the phased ultrasonic transducer array;
- a high voltage transmit pulser coupled to the transmit/receive switch; and
- a receive processor coupled to the transmit/receive switch, wherein the receive processor is integrated on an application specific integrated circuit (ASIC).

17. A configurable ultrasound imaging system, comprising:
- a phased ultrasonic transducer array including a plurality of transducer elements, each element configured to process an ultrasonic signal; and
- a portable, configurable processor configured to receive and process each of the ultrasonic signals corresponding to each of the transducer elements into an ultrasonic image, the portable, configurable processor comprising:
  - a transmit/receive switch coupled to the phased ultrasonic transducer array;
  - a high voltage transmit pulser coupled to the transmit/receive switch; and
  - a receive processor coupled to the transmit/receive switch, wherein the high voltage transmit pulser and the receive processor are integrated on an application specific integrated circuit (ASIC).

18. A configurable ultrasound imaging system, comprising:
- a phased ultrasonic transducer array including a plurality of transducer elements, each element configured to process an ultrasonic signal; and
- a portable, configurable processor configured to receive and process each of the ultrasonic signals corresponding to each of the transducer elements into an ultrasonic image, the portable, configurable processor comprising:
  - a transmit/receive switch coupled to the phased ultrasonic transducer-array;
  - a high voltage transmit pulser coupled to the transmit/receive switch;
  - a low voltage transmit timing signal; and
  - a receive processor coupled to the transmit/receive switch, wherein the high voltage transmit pulser and the low voltage transmit timing signal are integrated on an application specific integrated,circuit (ASIC).

19. The ultrasound imaging system of claim 1, having alternative imaging applications.

20. The ultrasound imaging system of claim 19, further comprising multiple beamforming modes and modifiable frequency.

21. The ultrasound imaging system of claim 20, further comprising swappable, plug-in transducers.

22. The ultrasound imaging system of claim 20, further comprising system clocks having modifiable frequency output.

23. The ultrasound imaging system of claim 1, further comprising alternative operating modes.

24. The ultrasound imaging system of claim 23, having alternative imaging modes.

25. The ultrasound imaging system of claim 24, wherein one of the alternative imaging modes is two-dimensional imaging.

26. The ultrasound imaging system of claim 24, wherein one of the alternative imaging modes is color flow mapping (cfm).

27. The ultrasound imaging system of claim 24, wherein one of the alternative imaging modes is angio processing.

28. The ultrasound imaging system of claim 24, wherein one of the alternative imaging modes is pulsed wave doppler imaging.

29. A configurable ultrasound imaging system, comprising:
- a phased ultrasonic transducer array including a plurality of transducer elements, each element configured to process an ultrasonic signal; and
- a portable, configurable processor configured to receive and process each of the ultrasonic signals corresponding to each of the transducer elements into an ultrasonic image, further comprising alternative operating modes having alternative aperture modes.

30. The ultrasound imaging system of claim 29, wherein one of the alternative aperture modes is full.

31. The ultrasound imaging system of claim 29, wherein one of the alternative aperture modes is split.

32. The ultrasound imaging system of claim 29, wherein the portable, configurable processor outputs a plurality of aperture modes.

33. The ultrasound imaging system of claim 1, having modifiable processing algorithms and operating features.

34. The ultrasound imaging system of claim 33, wherein the modifiable processing algorithms and operating features are implemented in software.

35. The ultrasound imaging system of claim 34, wherein the software is organized in a modular format.

36. The ultrasound imaging system of claim 34, wherein the software is updated using removable memory.

37. The ultrasound imaging system of claim 36, wherein the removable memory is scaleable.

38. The ultrasound imaging system of claim 34, wherein the software is updated using an external memory device.

39. A portable, configurable imaging system, comprising:
- a phased ultrasonic transducer array including a plurality of transducer elements, each element configured to process an ultrasonic signal; and
- a portable, configurable and scalable processor coupled to the phased ultrasonic transducer array and configured to receive and process each of the ultrasonic signals corresponding to each of the transducer elements into an ultrasonic image, wherein the phased ultrasonic transducer array and the configurable and scalable ultrasonic processor weigh less than eight (8) pounds.

* * * * *